United States Patent [19]

Strepparola et al.

[11] Patent Number: 5,395,657
[45] Date of Patent: Mar. 7, 1995

[54] PROCESS FOR IMPARTING OIL- AND WATER-REPELLENCY TO THE SURFACE OF POROUS CERAMIC MATERIALS

[75] Inventors: Ezio Strepparola, Treviglio; Viviana Boselli, Milan; Mauro Scapin, Busto Arsizio, all of Italy

[73] Assignee: Ausimont S.p.A., Milan, Italy

[21] Appl. No.: 168,712

[22] Filed: Dec. 16, 1993

[30] Foreign Application Priority Data

Dec. 16, 1992 [IT] Italy .................................. MI92A2860

[51] Int. Cl.$^6$ .............................................. B05D 3/02
[52] U.S. Cl. .................................. 427/393.6; 428/422; 428/540; 558/186
[58] Field of Search ...................... 427/393.6; 428/422, 428/540; 558/186

[56] References Cited

U.S. PATENT DOCUMENTS

| | | | |
|---|---|---|---|
| 3,188,340 | 6/1965 | Mackenzie | 260/461 |
| 3,242,218 | 3/1966 | Miller | 260/615 |
| 3,293,306 | 12/1966 | Le Bleu et al. | 260/615 |
| 3,492,374 | 1/1970 | LeBleu | 260/950 |
| 3,715,378 | 2/1973 | Sianesi et al. | 252/54 X |
| 3,810,874 | 5/1974 | Mitsch et al. | 260/75 H |
| 3,847,978 | 11/1974 | Sianesi et al. | 260/535 H |
| 4,085,137 | 4/1978 | Mitsch et al. | 526/11.1 X |
| 4,499,146 | 2/1985 | Piacenti et al. | 428/422 |
| 4,523,039 | 6/1985 | Lagow et al. | 568/615 |
| 4,745,009 | 5/1988 | Piacenti et al. | 427/393.5 |
| 4,746,550 | 5/1988 | Strepparola et al. | 427/385.5 |
| 4,814,372 | 3/1989 | Caporiccio et al. | 528/485 |
| 4,968,537 | 11/1990 | Leati et al. | 427/393.6 |
| 5,011,713 | 4/1991 | Leati et al. | 427/393.6 |
| 5,063,092 | 11/1991 | Leati et al. | 427/393.6 |

FOREIGN PATENT DOCUMENTS

| | | |
|---|---|---|
| 0148482A | 7/1985 | European Pat. Off. . |
| 0340740 | 11/1988 | European Pat. Off. . |
| 2413970 | 10/1974 | Germany . |
| 42-35908 | 8/1992 | Japan . |
| 50-39209 | 2/1993 | Japan . |
| 1104482 | 2/1968 | United Kingdom . |
| WO90/03357 | 4/1990 | WIPO . |

Primary Examiner—Michael Lusignan
Attorney, Agent, or Firm—Bryan Cave

[57] ABSTRACT

Oil- and water-repellency is imparted to the surface of a porous ceramic material, in particular of "cotto", by applying a phosphoric monoester having formula:

$$[R_f-O-CFY-L-O]_m P(O^-Z^+)_{3-m}$$

where:
L is a divalent organic group; m=1; Y is —F or —CF$_3$;
Z$^+$ is a cation; R$_f$ is a polyperfluoroalkylene oxide chain.

11 Claims, No Drawings

PROCESS FOR IMPARTING OIL- AND WATER-REPELLENCY TO THE SURFACE OF POROUS CERAMIC MATERIALS

The present invention relates to a process for imparting oil- and water-repellency to the surfaces of porous ceramic materials, and in particular of "cotto".

In the building industry, a broad use is made of porous cermic materials, which exhibit a dull and rather irregular surface, because after baking they were not subjected to vitrification and/or enamelling treatments. A typical example is the so-called "Tuscan cotto", which is generally utilized as flooring material. It is a ceramic obtained by baking in an oven a mixing of clayish materials mainly compoed of ores based on alumino-siiicates, such as illite, illite-smectite, kaolinite, chlorite, etc.

The porosity and the color, which are typical of this type of ceramics, are highly appreciated for aesthetical reasons, but they involve considerable difficulties as regards cleaning. In fact dirtiness, which can be carried by water or by oily substances, is easily absorbed and retained in the material pores, thereby causing a color alteration, and it is difficult to be removed by means of conventional washing techniques. The application of hydrocarbon-based waxes gives quite unsatisfactory results, as such products, although imparting an excellent water-repellency, exhibit a great affinity for oily products, wherefore, instead of repelling the fatty substances, favour the absorption of same.

It is known to use polyperfluoroalkylene oxides having perfluoroalkyl end groups for the protection of marble, stones, tiles, concrete and similar materials from the action of polluting atmospheric agents (see for example U.S. Pat. No. 4,499,146). Such products, besides imparting water- and oil-repellency properties, are endowed with a high permeability to gases and vapors, wherefore they permit to the protected material to "breathe". Furhtermore, thanks to a very low refraction index, the polyperfluoroalkylene oxides do not alter the aspect and original color of the material, since optical interference and/or reflection phenomena do not occur.

The presence of porosity in the material to be protected leads to migration phenomena of the polyperfluoroalkylene oxides from the surface to the interior of the material, with consequent decrease of the protective action in the course of time. A considerable improvement with respect to U.S. Pat. No. 4,499,146 is represented therefore by the use of polyperfluoroalkylene oxides functionalized with groups, which are capable of fixing the product to the substrate to be protected, such as carboxylic, estereal, amidic, hydroxylic, isocyanic, epoxy, silanic etc. groups, as is described in U.S. Pat. Nos. 4,745,009 and 4,746,550. Many other functionalized polyperfluoroalkylene oxides are described in U.S. Pat. No. 4,085,137.

On the basis of the tests carried out by the Applicant, most of the products described in the above-cited patents are not suited to solve the technical problen underlaying the present invention i.e. to provide products which are capable of:

(a) imparting a high water- and oil-repellency to the surface of porous cermic materials, and in particular to the surface of "cotto";

(b) remaining anchored to the surface of the treated material for a long time, in order not to cause migration to the interior of the same material and to withstand repeated washings with usual cleaners;

(c) not modifying the aesthetical characteristics of the treated material, in particular the color;

(d) being permeable to gases and vapors, in particular to water vapor;

(e) being applicable with economic methods, easy to be carried into practice.

The Applicant has now surprisingly found that the phosphoric monoesters derived from polyperfluoroalkylene oxides fully meet the above-listed requirements.

Thus, it is an object of the present invention to provide a process for imparting oil- and water-repellency to the surface of a porous ceramic material, which process comprises applying onto said surface, a phosphoric monoester having the formula:

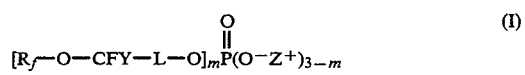

where:

L is a divalent organic group; $m=1$; Y is $-F$ or $-CF_3$; $Z^+$ is selected from: $H^+$; $M^+$ where M is an alkaline metal;

$N(R)_4^+$ where groups R, like or different from each other, are H or $C_1$–$C_6$ alkyls; $R_f$ is a polyperfluoroalkylene oxide chain.

A further object of the present invention are the phosphoric monoesters having formula (I) and the process for preparing them.

According to the process of the present invention, the phosphoric monoester of formula (I) can be optionally mixed with a phosphoric diester, corresponding to formula (I) where $m=2$, and/or a phosphoric triester, corresponding to formula (I), where $m=3$, in such amounts that the monoester content is at least equal to 80 mols-%.

By L is meant a divalent organic group, preferably non-fluorinated, which can be selected from:

(a) $-CH_2-(OCH_2CH_2)_n-$, where n is an integer from 0 to 3;

(b) $-CO-NR'-(CH_2)_q-$, where R' is H or a $C_1$–$C_4$ alkyl; q is an integer from 1 to 4.

Groups $R_f$ have preferably a number average molecular weight Mn ranging from 350 to 3,000, preferably from 400 to 1,000, and are composed of one or more repeating units randomly distributed along the chain and selected from: $(C_3F_6O)$; $(C_2F_4O)$; $(CFXO)$, where X is $-F$ or $-CF_3$; $(CYZ-CF_2CF_2O)$, where Y and Z, like or different from each other, are F, Cl or H.

Poly-perfluoroalkylene oxide chains $R_f$ can be selected in particular from the following classes:

where:

T is a (per)fluoroalkyl group selected from: $-CF_3$, $-C_2F_5$, $-C_3F_7$, $-CF_2Cl$, $-C_2F_4Cl$, $-C_3F_6Cl$; X is $-F$ or $-CF_3$; Z is $-F$, $-Cl$ or $-CF_3$; m and n are numbers such that the n/m ratio ranges from 0.01 to 0.5 and the molecular weight is in the above-indicated range;

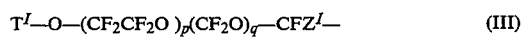

where:

$T^I$ is a (per)fluoroalkyl group selected from: —CF$_3$, —C$_2$F$_5$, —CF$_2$Cl, —C$_2$F$_4$Cl; $Z^I$ is —F or —Cl; p and q are numbers such that the q/p ratio ranges from 0.5 to 2 and the molecular weight is in the above indicated range;

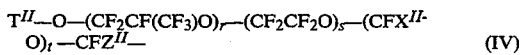
(IV)

where:
$T^{II}$ is a (per)fluoroalkyl group selected from: —CF$_3$, —C$_2$F$_5$, —C$_3$F$_7$, —CF$_2$Cl, —C$_2$F$_4$Cl, —C$_3$F$_6$Cl; $X^{II}$ is —F or —CF$_3$; $Z^{II}$ is —F, —Cl or —CF$_3$; r, s and t are numbers such that r+s ranges from 1 to 50, the t/(r+s) ratio ranges from 0.01 to 0.05 and the molecular weight is in the above indicated range;

(V)

where:
$T^{III}$ is —C$_2$F$_5$ or —C$_3$F$_7$; u is a number such that the molecular weight is in the above indicated range;

(VI)

where:
Y and Z, like or different from each other, are F, Cl or H; $T^{IV}$ is —CF$_3$, —C$_2$F$_5$ or —C$_3$F$_7$; v is a number such that the molecular weight is in the above indicated range;

(VII)

where:
$T^V$ is —CF$_3$ or —C$_2$F$_5$; w is a number such that the molecular weight is in the above indicated range.

The phosphoric monoester of formula (I) can be utilized either in acid form (Z=H$^+$), or salified with an alkaline metal hydroxide (Z=M$^+$, where M=Li, Na, K, etc.), or with ammonia or with an amine (Z=N(R)$_4$$^+$). Groups R can be optionally substituted by hydroxyls or they can be linked to one another so as to form a ring on the nitrogen atom, for example of the morpholinic type.

The amount of phosphoric monoester of formula (I) to be utilized in order to obtain an effetive water- and oil-repellency action varies over a very wide range as a function of the surface characteristics of the material to be treated and of the molecular weight of the monoester itself. For example, for a typical "Tuscan cotto" there are applicable about 0.5 mg/cm$^2$ of a product of formula (I) having a R$_f$ chain with Mn=700. As a function of the specific conditions, for those skilled in the art it is sufficient to carry out a few tests for determining the optimum amount to be applied.

The monoester of formula (I) is preferably applied in the form of solution, at concentrations generally ranging from 0.1 to 5% by weight, preferably from 0.5 to 2% by weight.

Suitable solvents, or mixtures of solvents, can be selected from the following classes: aliphatic alcohols having 1 to 4 carbon atoms, fluorocarbons and chlorofluorocarbons, optionally containing hydrogen, ketones and esters having 3 to 10 carbon atoms, methylchloroform, low molecular weight (generally from 400 to 1,000) polyperfluoroalkylene oxide having fluoroalkyl end groups, etc. It is possible to use also solvent/non-solvent mixtures such as, for example, ketone/water mixtures or alcohols/water mixtures in ratios ranging from 10:90 to 90:10 by volume, or also (chloro)fluorocarbons/dimethylformamide mixtures or methylchloroform/dimethylformamide mixtures in ratios ranging from 1:1 to 3:1 by volume.

The choice of the most suitable solvent depends on several factors. First of all, the solvent must be capable of dissolving, in the desired concentration, the specific product of formula (I) which is to be utilized. To this end it is sufficient to carry out some solubility tests.

Furthermore, the solvent must quickly dry, leaving the treated surface free from halos. In order to check whether the selected solvent meets this requirement, the following test can be conducted. 20 ml of solvent are dropped onto a "Tuscan cotto" tile having a surface of 450 cm$^2$; two hours after the application, at room temperature (25° C.) the "cotto" surface must be dry and free from halos.

The solvent suitability shall be further checked by applying onto a "Tuscan cotto" test piece, a solution composed of the solvent to be tested and of the product of formula (I) to be utilized, at the desired concentration. The surface so treated is subjected to a water-repellency test according to the method described later on herein. The solvent is to be considered as suitable if a sphericity index ranging from A to C is obtained (see the scale reported later on herein) and no dark halo appears at the base of the water drop (which halo indicates the absorption begin) in the ten minutes following the deposition of the drop. This additional test in order to check the solvent suitability is particularly important when it is desired to utilize solvent/non-solvent mixtures. In these cases, in fact, the solvent could evaporate too soon as compared with the non-solvent, thereby causing a non-uniform distribution of the product on the treated surface.

The phosphoric monoesters of formula (I) are preparable by reacting the corresponding hydroxy-terminated polyperfluoroalkylene oxides R$_f$—O—CFY—L—OH with POCl$_3$ in such molar ratios that POCl$_3$ is always in great excess. Generally, the POCl$_3$/hydroxy-terminated product molar ratio ranges from 5:1 to 10:1, preferably from 6:1 to 8:1. The reaction is conducted by gradually dropping the hydroxy-terminated product into POCl$_3$, in the presence of a base, for example a tertiary amine, such as pyridin, triethylamine, tributylamine, at a temperature generally ranging from 50° to 100° C., preferably from 70° to 90° C. The reaction is conducted, always under stirring, until disappearance of the hydroxylic groups, what can be checked by infrared analysis. The POCl$_3$ excess is removed by distillation and the resulting product is hydrolized with water or with dilute hydrochloric acid. The organic phase is separated by extraction with a proper water-insoluble solvent, for example a (chloro)fluorocarbon or methylchloroform. The separation is preferably carried out in the presence of a co-solvent, for example a water-soluble ketone, which has the function of preventing the formation of emulsions, which would hinder the separation of the organic product. From the organic phase, the product is separated according to conventional techniques, such as, for example, evaporation of the solvent.

From such reaction, the monoesters are obtained with high yields, usually in admixture with minor amounts of the corresponding di- and tri-esters.

The hydroxy-terminated polyperfluoroalkylene oxides R$_f$—O—CFY—L—OH are known products and are preparable according to known methods starting from the corresponding polyperfluoroalkylene oxides having —COF end groups. The starting polyperfluoroalkylene oxides containing end groups —COF are described, for example, in patents: GB-1,104,482 (class (a)), U.S. Pat. No. 3,715,378 (class (b)), U.S. Pat. No. 3,242,218 (class (c)), U.S. Pat. No. 3,242,218 (class (d)), EP-148,482 (class (e)), U.S. Pat. No. 4,523,039 (class (f)), or also in patent application EP-340,740 and WO 90/03357.

In particular, products $R_f$—O—CFY—L—OH, where L=—$CH_2(OCH_2CH_2)_n$— can be prepared by reduction of the corresponding fluorinated acids and, when n≠0, by subsequent ethoxylation reaction with ethylene oxide, conforming to what is described, for example, in patents: U.S. Pat. No. 3,293,306, U.S. Pat. No. 3,847,978, U.S. Pat. No. 3,810,874 and U.S. Pat. No. 4,814,372.

The products where L=—CO—NR'—$(CH_2)_q$— are preparable by reacting the corresponding acyl fluorides with an alkanol-amine of formula R'—NH—$(CH_2)_q$—OH.

The monophosphoric acids utilized in the process of the present invention, besides imparting a particularly high oil- and water-repellency degree, are also capable of stably anchoring to the substrate, whereby no migration phenomena to the substrate interior have been observed. Furthermore, the treated surface retains the oil- and water-repellency characteristics even after repeated washings with the most common cleaners.

The present invention will be now described more in detail by the following examples, which are given merely for purposes of illustration and are not intended to limit the scope of the invention.

The oil- and water-repellency degrees have been determined by observing the behaviour of an oil drop or water drop deposited onto the treated surface, taking two distinct parameters into consideration: drop sphericity and absorption time.

The drop sphericity is in itself a measure of the liquid repellency, and it can be determined by measuring the contact angle, i.e. the angle formed by the substrate plane and by the tangent to the the drop surface in the point of contact with said plane. A perfectly spheric drop has a contact angle of 180°, while a flat drop has a contact angle tending to 0°.

Due to the irregularity of the "Tuscan cotto" surface, an accurate measurement of the contact angle is practically impossible, wherefore to discrete intervals of contact angle, a sphericity index according to the following scale has been correlated:

| Sphericity index | Contact angle |
|---|---|
| A | about 180° |
| B | 150°–180° |
| C | 120°–150° |
| D | 90°–120° |
| E | <90° |

A perfectly spheric drop, which has a practically punctiform contact surface has a sphericity index A; nearly perfectly spheric drops, having an extremely reduced, but not punctiform surface contact surface, have been classified with B; index C has been attributed to drops exhibiting a good sphericity, having a rather wide contact surface, but always smaller than the dimensions of the drop. At D and E, the contact angle furtherly decreases and, correspondingly, the contact surface increases. The values reported in the examples represent an average calculated on 20 drops, having a volume of about 3/ul and deposited onto 25 cm² of "Tuscan cotto". For the water-repellency test, demineralized water has been utilized, while for the oil-repellency test, a paraffin oil having a viscosity of 20 cSt (commercial product: ESSO P60 ®) was utilized.

A correct evaluation of the liquid-repellency degree must take another parameter into account, namely the complete absorption time of the drop by the treated material surface (hereinafter referred to as t). Of course, in the case of water (water-repellency), the drop volume decreases in the time also due to the evaporation, wherefore there is a maximum time limit, within which the evaluation is still possible. At room temperature, for a water drop of 3/ul, a maximum limit of 30 minutes has been fixed. In the case of oil (oil-repellency), the evaporation is quite negligible, wherefore the maximum limit has been arbitrarily fixed at 7 days.

The begin of the absorption, if any, is indicated by the appearance of a dark halo at the drop base, which halo extends in the course of time and is accompanied by a proportional reduction of the drop volume.

The evaluation scale of the absorption index has been fixed as follows:

| Absorption index | t Water (min.) | Oil (hours) |
|---|---|---|
| a | 0 | 0 |
| b | 2,5 | 1 |
| c | 5 | 2 |
| d | 10 | 3 |
| e | 15 | 4 |
| f | 20 | 5 |
| g | 25 | 6 |
| h | 30 | 24 |
| i | —(*) | —(*) |

(*)absence of absorption.

Both for the water-repellency and for the oil-repellency, the dark halo appears within 5 minutes after the drop deposition at absorption indexes from (a) to (d), within 10 minutes at indexes from (e) to (h). No halo appears at absorption index (i).

In like manner as for the sphericity index, the values reported in the examples are the average calculated on 20 drops having a volume of about 3/ul and deposited on 25 cm² of "Tuscan cotto".

On the basis of the sphericity index and absorption index determined according to the criteria described hereinabove, the following evaluation scale has been fixed, which is valid for both the oil-repellency and the water-repellency:

| Oil- or water-repellency | Sphericity index | Absorption index |
|---|---|---|
| 0 | E | a |
| 1 | E | b |
| 2 | E | c |
| 3 | E | d |
| 4 | E | e |
| 5 | E | f |
| 6 | E | g |
| 7 | D | h |
| 8* | E | i |
| 8 | C | i |
| 9 | B | i |
| 10 | A | i |

EXAMPLE 1

Onto a "Tuscan cotto" tiles measuring 5×5 cm it was dropped 1 ml of a solution, at 1% by weight in isopropanol, of a mixture consisting for 90 mols-% of a phosphoric monoester corresponding to formula (I) with: L=—CH$_2$(OCH$_2$CH$_2$)—; m=1; Z$^+$=H$^+$; R$_f$ is a chain of Galden ® Y (formula (II)), having Mn=700, Mw/Mn=1.3, m/n =20. The remaining 10% consisted of a mixture of the corresponding diester (m=2) and triester (m=3).

The "cotto" was allowed to dry at room temperature for 2 hours, Then the water- and oil-repellency was evaluated conforming to the method described hereinbefore. The values are reported in Table I.

The applied product was obtained as follows. 200 g (0.277 mols) of the corresponding hydroxy-terminated Galden® Y were gradually dropped (in 4 hours) into 225 g of POCl$_3$ (POCl$_3$/Galden molar ratio=6:1). The reaction was maintained under stirring for one hour or more. During all the reaction time, the temperature was maintained at 90° C. The POCl$_3$ excess was then distilled off (at 50° C./20 mm Hg). The distillation residue was then hydrolized by addition of 60 ml of H$_2$O. After addition of 90 ml of A113 (CF$_2$Cl—CFCl$_2$) and of 35 ml of acetone, the organic phase was separated in an extraction funnel. The product contained in the organic phase was dried by evaporation of the solvents (at 80° C./1 mbar). There were obtained 192 g of a product consisting for 90 mols-% of monoester and for 10 mols-% of di- and tri-ester, as it was checked by acidimetric titration and $^{31}$P-NMR analysis.

EXAMPLES 2-3

Example 1 was repeated under the same conditions and with the same product utilizing solutions in isopropanol at 2.5% by weight (Ex. 2) and at 5.0% by weight (Ex. 3). The oil- and water-repellency values are reported in Table I.

EXAMPLES 4-6

Example 1 was repeated under the same conditions and with the same product, using as a solvent an isopropanol/water mixture in a 20:80 ratio by volume. Solutions at a concentration of 1.0% (Ex. 4), 2.5% (Ex. 5) and 5.0% (Ex. 6) by weight were applied. The water- and oil-repellency values are reported in Table I.

EXAMPLE 7-8

Example 1 was repeated under the same conditions and with the same product, utilizing as a solvent an isopropanol/water mixture in a 50:50 ratio by volume. Solutions at a concentration of 2.5% (Ex. 7) and 5.0% (Ex. 8) by weight were applied. The water- and oil-repellency values are reported in Table I.

EXAMPLES 9-10

Example 1 was repeated under the same conditions and with the same product, utilizing as a sol vent a water/glycol isopropanol mixture in a 69:17:14 ratio by volume. Solutions at a concentration of 2.5% (Ex. 9) and 5.0% (Ex. 10) by weight were applied. The water- and oil-repellency values are reported in Table I.

EXAMPLES 11-12

Example 1 was repeated under the same conditions and with the same product, using as a solvent a water/glycol/isopropanol mixture in a 75:8:17 ratio by volume. Solutions at a concentration of 2.5% (Ex. 11) and 5.0% (Ex. 12) by weight were applied. The water- and oil-repellency values are reported in Table I.

EXAMPLE 13

Example 1 was repeated utilizing a solution, at 1% by weight in isopropanol, of a mixture composed for 90 mols-% of a phosphoric monoester corresponding to formula (I) where: L=—CH$_2$(OCH$_2$CH$_2$)—; m=1; Z$^+$=H$^+$; R$_f$ is a chain of Galden ® Y (formula (II)), having Mn=900, Mw/Mn=1.0, m/n=20. The remaining 10% was composed of the corresponding diester (m=2) and triester (m=3). The product was prepared according to the same method described in Example 1. The water- and oil-repellency values are reported in Table II.

EXAMPLE 14-15

Example 1 was repeated utilizing solutions, at 0.5% (Ex. 14) and 1.0% (Ex. 15) by weight in isopropanol, of a mixture composed for 90 mols-% of a phosphoric monoester corresponding to formula (I) where: L=—CH$_2$(OCH$_2$CH$_2$)—; m=1; Z$^+$=H$^+$; R$_f$ is a chain of Galden® Y (formula (II)), having Mn=400, Mw/Mn=1.0, m/n=20. The remaining 10% consisted of the corresponding diester (m=2) and triester (m=3). The product was prepared according to the same method described in Example 1. The water- and oil-repellency values are reported in Table II.

EXAMPLE 16

The phosphoric monoester of example 13 was salified with a hydroalcoholic KOH solution in a stoichiometric amount. After removal of the solvent by evaporation, the product was dissolved in A113 in such amount as to obtain a solution at 1% by weight. Such solution was applied on a "Tuscan cotto" according to the modalities described in Example 1. The water- and oil-repellency values are reported in Table II.

EXAMPLE 17 (Comparative)

Example 1 was repeated utilizing a solution, at 1% by weight in isopropanol, of a product of formula:

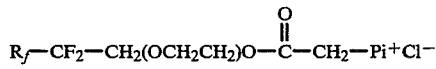

where Pi is a pyridinic ring, R$_f$ is a chain of Galden ® Y (formula (II)), with Mn=700 and Mw/Mn=1.3 and m/n=20.

Such product was obtained—according to what is described in Italian patent application No. 360/MI92A, filed on Feb. 20, 1992 by the Applicant—by esterification reaction of the hydroxy-derivative of formula: R$_f$—CF$_2$—CH$_2$(OCH$_2$CH$_2$)OH with chloroacetic acid, and subsequent quaternization with pyridinin in isopropanol.

The water- and oil-repellency values are reported in Table III.

EXAMPLE 18 (Comparative)

Example 1 was repeated utilizing a solution at 5% by weight in A113 of a mixture composed of R$_f$—COO$^-$ TEA$^+$ (TEA=Triethanolamine) and of the corresponding ketone R$_f$—CO—CF$_3$, in a 1:2 molar ratio, where R$_f$ is a chain of Galden ® Y (formula (II)), having Mn=2700, Mw/Mn=1.3 and m/n=35. Such mixture was obtained, according to conventional techniques, by acid hydrolysis and subsequent salification with TEA of the product deriving from the thermal treatment (200°-250° C.) of the rough product resulting from the photooxidation of hexafluoropropene with $O_2$.

The water- and oil-repellency values are reported in Table III.

EXAMPLE 19 (Comparative)

Example 1 was repeated using a solution at 1% by weight in isopropanol of a product of formula:

$$R_f\text{—CO—NH—}(CH_2)_3\text{—Si}(OC_2H_5)_3$$

where $R_f$ is a chain of Galden ® y (formula (II)), having Mn=700, Mw/Mn=1.3 and m/n=20. Such product was obtained by reacting the corresponding acyl-derivative with 3-amino-propyl-triethoxysilane.

The water- and oil-repellency values are reported in Table III.

EXAMPLE 20 (Comparative)

Example 1 was repeated utilizing a solution at 1% by weight in A113 of a non-functionalized Galden ® Y, corresponding to formula (II) with $CF_3$ end group, having Mn=1,500, obtained via fractional distillation of the corresponding commercial product.

The water- and oil-repellency values are reported in Table III.

EXAMPLE 21 (Comparative)

Example 1 was repeated utilizing a solution at 1% by weight in A113 of a product of formula:

$$R_f\text{—}CH_2(OCH_2CH_2)_6\text{—OH}$$

where $R_f$ is a chain of Galden ® Y (formula (II)), having Mn=700, Mw/Mn=1.3 and m/n=20. Such product was obtained by reduction of the corresponding Galden ® Y having —COF end groups and by subsequent ethoxylation with ethylene oxide.

The water- and oil-repellency values are reported in Table III.

EXAMPLE 22 (Comparative)

Example 1 was repeated utilizing a solution at 4% by weight in A113 of a product of formula:

$$R_f\text{—CO—OH}$$

in admixture with a ketone of formula:

$$R_f\text{—CO—}CF_3$$

where $R_f$ is a chain of Galden ® Y (formula (II)), having Mn=2,700, Mw/Mn=1.3 and m/n=35. The acid/ketone molar ratio of aboit 1:2. It was the same product utilized in Example 18, but not subjected to salification with TEA.

The water- and oil-repellency values are reported in Table III.

EXAMPLE 23 (Comparative)

Example 1 was repeated utilizing a solution at 1% by weight in A113 of a product of formula:

$$R_f\text{—COOH}$$

where $R_f$ is a chain of Galden ® Y (formula (II)), having Mn=700, Mw/Mn=1.3 and m/n=20. Such product was obtained by hydrolysis of the corresponding Galden ® Y having —COF end groups.

The water- and oil-repellency values are reported in Table III.

EXAMPLE 24 (Comparative)

Example 1 was repeated utilizing a solution at 1% by weight in A113 of a product of formula:

$$R_f\text{—COOH}$$

where $R_f$ is a chain of Galden ® Y (formula (II)), having Mn=2,700, Mw/Mn=1.3 and m/n=35, obtained from the product utilized in Example 22 by selective precipitation of the acids as calcium salts and by subsequent acidification.

The water- and oil-repellency values are reported in Table III.

EXAMPLE 25 (Comparative)

Example 1 was repeated utilizing a solution at 1% by weight in A113 of a product of formula:

$$R_f\text{—}CH_2OH$$

where $R_f$ is a chain of Galden ® Y (formula (II)), having Mn=700, Mw/Mn=1.3 and m/n=20. Such product was obtained by reduction of the corresponding Galden ® Y having —COF end groups.

The water- and oil-repellency values are reported in Table III.

EXAMPLE 26 (Comparative)

Example 1 was repeated utilizing a solution at 1% by weight in A113 of a product of formula:

$$R_f\text{—}CH_2OCH_2CH_2\text{—OH}$$

where $R_f$ is a chain of Galden ® Y (formula (II)), having Mn=700, Mw/Mn=1.3 and m/n=20. Such product was obtained by reduction of the corresponding Galden ® Y having —COF end groups and by subsequent ethoxylation with ethylene oxide.

The water- and oil-repellency values are reported in Table III.

EXAMPLE 27 (Comparative)

Example 1 was repeated utilizing a solution at 1 % by weight in water of Surflon ® S-112 (salified perfluoroalkyl phosphate) produced by Asahi Glass Co..

The water- and oil-repellency values are reported in Table III.

TABLE I

| EX. | SOLVENT | CONC. (% by wg.) | WATER-REPELLENCY | OIL-REPELLENCY |
|---|---|---|---|---|
| 1 | isopropanol | 1.0 | 8 | 8 |
| 2 | " | 2.5 | 8 | 8 |
| 3 | " | 5.0 | 8 | 8 |
| 4 | isoprop./$H_2O$ | 1.0 | 9 | 8 |

TABLE I-continued

| EX. | SOLVENT | CONC. (% by wg.) | WATER-REPELLENCY | OIL-REPELLENCY |
|---|---|---|---|---|
| 5 | isoprop./H$_2$O 20/80 | 2.5 | 9 | 8 |
| 6 | isoprop./H$_2$O 20/80 | 5.0 | 9 | 8 |
| 7 | isoprop./H$_2$O 50/50 | 2.5 | 8 | 8 |
| 8 | isoprop./H$_2$O 50/50 | 5.0 | 9 | 8 |
| 9 | H$_2$O/glyclol/isoprop. 69/17/14 | 2.5 | 8 | 8 |
| 10 | H$_2$O/glyclol/isoprop. 69/17/14 | 5.0 | 8 | 8 |
| 11 | H$_2$O/glyclol/isoprop. 75/8/17 | 2.5 | 8 | 8 |
| 12 | H$_2$O/glyclol/isoprop. 75/8/17 | 5.0 | 8 | 8 |

TABLE II

| EX. | SOLVENT | CONC. (% by wg.) | WATER-REPELLENCY | OIL-REPELLENCY |
|---|---|---|---|---|
| 13 | isopropanol | 1.0 | 9 | 8 |
| 14 | " | 0.5 | 8 | 8 |
| 15 | " | 1.0 | 8 | 8 |
| 16 | A113 | 1.0 | 9 | 8 |

TABLE III
(Comparative Examples)

| EX. | PRODUCT | WATER-REPELLENCY | OIL-REPELLENCY |
|---|---|---|---|
| 17 | R$_f$CF$_2$CH$_2$OCH$_2$CH$_2$O—CO—CH$_2$—Pi$^+$Cl$^-$ | 0 | 7 |
| 18 | R$_f$—COO$^-$TEA$^+$ + R$_f$—CO—CF$_3$ | 2 | 7 |
| 19 | R$_f$—CO—NH—(CH$_2$)$_3$—Si(OC$_2$H$_5$)$_3$ | 0 | 3 |
| 20 | R$_f$—CF$_3$ | 0 | 0 |
| 21 | R$_f$—CH$_2$(OCH$_2$CH$_2$)$_6$—OH | 0 | 7 |
| 22 | R$_f$—CO—OH + R$_f$—CO—CF$_3$ | 0 | 3 |
| 23 | R$_f$—COOH | 0 | 6 |
| 24 | R$_f$—COOH | 0 | 8* |
| 25 | R$_f$—CH$_2$OH | 0 | 6/7 |
| 26 | R$_f$—CH$_2$OCH$_2$CH$_2$OH | 0 | 8* |
| 27 | (C$_n$F$_{2n+1}$)$_m$—PO—(O$^-$Z$^+$)$_{3-m}$ | 2 | 8 |

We claim:

1. A process for imparting oil- and water-repellency to the surface of a porous ceramic material, which comprises applying onto said surface a phosphoric monoester of formula:

$$[R_f-O-CFY-L-O]_m P(O^-Z^+)_{3-m} \quad (I)$$

where:

L is a divalent organic group; m=1; Y is —F or —CF$_3$; Z$^+$ is selected from: H$^+$; M$^+$ where M is an alkaline metal; N(R)$_4$$^+$ where groups R, like or different from one another, are H or C$_1$-C$_6$ alkyls; R$_f$ is a polyperfluoroalkylene oxide chain.

2. The process of claim 1, wherein the phosphoric monoester of formula (I) is mixed with a phosphoric diester, corresponding to formula (I) where m=2, and/or a phosphoric triester, corresponding to formula (I) where m=3, in such amounts that the monoester content is at least equal to 80 mols-%.

3. The process of claim 1, wherein group L is selected from:
    (a) —CH$_2$—(OCH$_2$CH$_2$)$_n$—, where n is an integer ranging from 0 to 3;
    (b) —CO—NR'—(CH$_2$)$_q$—, where R' is H or a C$_1$-C$_4$ alkyl; q is an integer ranging from 1 to 4.

4. The process of claim 1, wherein the R$_f$ chains are composed of one or more repeating units, statistically distributed along the chain, selected from: (C$_3$F$_6$O); (C$_2$F$_4$O); (CFXO), where X is —F or —CF$_3$; (CY-Z—CF$_2$CF$_2$O), where Y and Z, like or different from each other, are F, Cl or H; and have a number average molecular weight ranging from 350 to 3,000.

5. The process of claim 4, wherein the R$_f$ chains have a number average molecular weight ranging from 400 to 1,000.

6. The process of claim 4, wherein the R$_f$ chains are selected from the following classes:

$$\text{(a) } T-O-(CF_2CF(CF_3)O)_m(CFXO)_n-CFZ- \quad (II)$$

where:

T is a (per)fluoroalkyl group selected from: —CF$_3$, —C$_2$F$_5$, —C$_3$F$_7$, CF$_2$Cl, —C$_2$F$_4$Cl, —C$_3$F$_6$Cl; X is —F or —CF$_3$; Z is —F, —Cl or —CF$_3$; m and n are numbers such that the n/m ratio ranges from 0.01 to 0.5 and the molecular weight is in the above-indicated range;

$$\text{(b) } T^I-O-(CF_2CF_2O)_p(CF_2O)_q-CFZ^I- \quad (III)$$

where:

T$^I$ is a (per)fluoroalkyl group selected from: —CF$_3$, —C$_2$F$_5$, —CF$_2$Cl, —C$_2$F$_4$Cl; Z$^I$ is —F or —Cl; p and q are numbers such that the q/p ratio ranges from 0.5 to 2 and the molecular weight is in the above indicated range;

(c)
$$T^{II}-O-(CF_2CF(CF_3)O)_r-(CF_2CF_2O)_s-(CFX^{II}O)_t-CFZ^{II}- \quad (IV)$$

where:
$T^{II}$ is a (per)fluoroalkyl group selected from: $-CF_3$, $-C_2F_5$, $-C_3F_7$, $-CF_2Cl$, $-C_2F_4Cl$, $-C_3F_6Cl$; $X^{II}$ is $-F$ or $-CF_3$; $Z^{II}$ is $-F$, $-Cl$ or $-CF_3$; s and t are numbers such that $r+s$ ranges from 1 to 50, the $t/(r+s)$ ratio ranges from 0.01 to 0.05 and the molecular weight is in the above indicated range;

(d) $T^{III}-O-(CF(CF_3)CF_2O)_u-CF(CF_3)- \quad (V)$ where:
$T^{III}$ is $-C_2F_5$ or $-C_3F_7$; u is a number such that the molecular weight is in the above indicated range;

(e) $T^{IV}-O-(CYZ-CF_2CF_2O)_v-CYZ-CF_2- \quad (VI)$ where:
Y and Z, like or different from each other, are F, Cl or H; $T^{IV}$ is $-CF_3$, $-C_2F_5$ or $-C_3F_7$; v is a number such that the molecular weight is in the above indicated range;

(f) $T^V-O-(CF_2CF_2O)_w-CF_2- \quad (VII)$ where:
$T^v$ is $-CF_3$ or $-C_2F_5$; w is a number such that the molecular weight is in the above indicated range.

7. The process of claim 1, wherein the phosphoric monoester is applied in the form of a solution at a concentration ranging from 0.1 to 5% by weight.

8. The process of claim 7, wherein the phosphoric monoester is applied in the form of a solution in a solvent selected from: aliphatic alcohols having 1 to 4 carbon atoms, fluorocarbons and chlorofluorocarbons optionally containing hydrogen, ketones and esters having 3 to 10 carbon atoms, methylchloroform, low molecular weight polyperfluoroalkylene oxides having fluoroalkyl end groups, or mixtures thereof.

9. The process of claim 7, wherein the phosphoric monoester is applied in the form of a solution in a solvent/non-solvent mixture selected from the group consisting of ketone/water, alcohols/water, (chloro)fluorocarbons/dimethylformamide, and methylchloroform/dimethyl-formamide.

10. Phosphoric monoesters having the formula:

$$[R_f-O-CFY-L-O]_m P(O^-Z^+)_{3-m} \quad (I)$$

where:
L is a divalent organic group; m=1, Y is $-F$ or $-CF_3$; $Z^+$ is selected from :$H^+$; $M^+$ where M is an alkali metal; $N(R)_4^+$ where groups R, like or different from one another, are H or $C_1-C_6$ alkyls; $R_f$ is a polyperfluoroalkylene oxide chain.

11. The process for preparing the phosphoric monoesters of claim 10, which comprises reacting, in the presence of a base, the corresponding hydroxy-terminated polyperfluoroalkylene oxides $R_f-O-CFY-L-OH$ with $POCl_3$, in such amount that the $POCl_3$/hydroxy-terminated product molar ratio ranges from 5:1 to 10:1.

* * * * *

UNITED STATES PATENT AND TRADEMARK OFFICE
CERTIFICATE OF CORRECTION

PATENT NO. : 5,395,657

DATED : March 7, 1993

INVENTOR(S): Ezio Strepparola et al.

It is certified that error appears in the above-identified patent and that said Letters Patent is hereby corrected as shown below:

In claim 19, column 14, lines 20-22 should read:

$$[R_f-O-\overset{\underset{\|}{O}}{C}FY-L-O]_m P(O^-Z^+)_{3-m}$$

Signed and Sealed this

Twenty-seventh Day of June, 1995

Attest:

BRUCE LEHMAN

Attesting Officer     Commissioner of Patents and Trademarks